United States Patent [19]
Schroeppel

[11] Patent Number: 5,876,429
[45] Date of Patent: Mar. 2, 1999

[54] METHODS AND DEVICES FOR IN VIVO REPAIR OF CARDIAC STIMULATOR LEADS

[75] Inventor: Edward A. Schroeppel, Lake Jackson, Tex.

[73] Assignee: Intermedics, Inc., Angleton, Tex.

[21] Appl. No.: 472,518

[22] Filed: Jun. 7, 1995

[51] Int. Cl.$^6$ ...................................................... A61N 1/05
[52] U.S. Cl. .......................................... 607/115; 128/898
[58] Field of Search ................................... 128/642, 641, 128/898; 607/115, 116, 119, 122, 123, 132; 606/198; 623/1, 11, 12

[56] References Cited

U.S. PATENT DOCUMENTS

| | | | |
|---|---|---|---|
| 4,711,975 | 12/1987 | Morel et al. | 174/93 |
| 4,902,856 | 2/1990 | Miller | 174/93 |
| 5,273,053 | 12/1993 | Pohndorf | 607/132 |
| 5,342,348 | 8/1994 | Kaplan | 606/198 |
| 5,350,419 | 9/1994 | Bendel et al. | 607/119 |
| 5,405,377 | 4/1995 | Cragg | 606/198 |
| 5,423,763 | 6/1995 | Helland et al. | 128/654 |
| 5,476,493 | 12/1995 | Muff | 607/119 |
| 5,540,712 | 7/1996 | Kleshinski et al. | 606/198 |

OTHER PUBLICATIONS

Associated Press News Item dated Jan. 24, 1995, entitled "Gov't Urges Pacemaker Exams," 2 pages.

Nallamothu, No., et al., "Lead–Related Morbidity in Patients with Cardioverter–Defibrillators Utilizing Non–Thoracotomy Lead Systems," *PACE*, vol. 17, No. 4, Part II, p. 761 (NASPE 1994 Abstracts).

"The Cook Pacemaker Lead Extraction System," product information of Cook Pacemaker Corporation, Leechburg, PA, dated Jul. 1993, 4 pages.

Hayes, D.L. et al., *Dictionary of Cardiac Pacing Electrophysiology and Arrythmias*, Peritus Corp., Miami Lakes, 1993, pp. 133–134.

Brinker, J., "Endocardial Pacing Leads: The Good, the Bad, and the Ugly," *PACE*, vol. 18, May 1995, Part I., pp. 953–954.

Parsonnet, V., "The Retention Wire Fix," *PACE*, vol. 18, May 1995, Part I, pp. 955–956.

Lloyd, M., et al., "Atrial 'J' Pacing Lead Retention Wire Fracture: Radiographic Assessment, Incidence of Fracture, and Clinical Management," *PACE*, vol. 18, May 1995, Part I, pp. 958–964.

Byrd, C., "Management of Implant Complications," In, K.A. Ellenbogen et al. *Clinical Cardiac Pacing*, W.B. Saunders, Philadelphia, 1995, pp. 491–522.

Anderson, H., et al., "Mechanical Devices," In Willerson and Cohn, *Cardiovascular Medicine*, Churchill Livingstone, New York 1995, pp. 636–644.

*Primary Examiner*—Robert L. Nasser
*Attorney, Agent, or Firm*—Conley, Rose & Tayon, P.C.

[57] ABSTRACT

The present invention provides devices and methods for using such devices which can be positioned over cardiac stimulator lead sections which are known to be flawed or which are at risk of failure, such as wire stiffener fractures and electrical shorts. The devices and methods of the invention can protect a patient with an implanted cardiac stimulator whose flawed lead represents a threat to his health or life. The devices and methods of use of the invention provide movable sleeves which can be positioned at various points along the length of a lead at the discretion of the heart surgeon.

29 Claims, 6 Drawing Sheets

METHODS AND DEVICES FOR IN VIVO REPAIR OF CARDIAC STIMULATOR LEADS

BACKGROUND OF THE INVENTION

A. Field of the Invention

The invention relates to devices and methods for repairing or maintaining the integrity of cardiac stimulator leads. In particular, the devices and methods disclosed as useful in the repair or maintenance of such leads are configured as sleeves which can be positioned over a section of lead in need of repair.

B. Description of the Related Art

Endocardial leads have become the standard for both pacing and cardioversion/defibrillation implantable cardiac stimulators. These leads typically exhibit a long implantation life. However, failures do occur. Brinker, "Endocardial Pacing Leads: The Good, the Bad, and the Ugly," PACE, Vol. 18, May 1995, Part I, Pg. 953 et seq.

Failure may result from a breach of lead integrity (insulation, wire stiffener, or conductor), or an uncoupling of the electrode-myocardial interface caused by tip displacement. In the pacemaker-dependent patient, lead failure can result in significant morbidity and even death.

Considerable attention has recently been directed to breaches in the integrity of polyurethane insulation used for pacing leads. The use of this material resulted in the development of smaller diameter leads than were previously possible with traditional silicone rubber materials. Unfortunately, certain lead models using Pellethane™ (Dow Chemical) 80A polyurethane exhibited failure resulting from degradation of the insulation due to environmental stress cracking and metal ion oxidation. Insulation failure may not be recognized until years after market release. In situs detection of insulation failure is difficult and requires careful monitoring. Parsonnet, "The Retention Wire Fix," PACE, Vol. 18, May 1995, Part I, Pg. 955 et seq.

In certain leads, a small (3.5 inches long, 0.013 inches wide, and 0.0065 inches thick) metal J-shaped retention ribbon located beneath the outer insulation may fracture and erode through the insulation. This protruding metal fragment may puncture the heart and has been associated with the death of patients and pericardial tamponade in others. Although these types of products have been recalled, some 40,000 leads had already been utilized worldwide, over half of which were implanted in the United States prior to 1994. Screening such leads by fluoroscopy has revealed signs of retention wire fracture in about 12% of patients. Lloyd, "Atrial 'J' Pacing Lead Retention Wire Fracture: Radiographic Assessment, Incidence of Fracture, and Clinical Management, " PACE, Vol. 18, May 1995, Part I, Pg. 958 et seq.

Prior techniques and devices used with patients with lead failure usually involved implantation of a new lead, and optionally extracting the problem lead. While atrial lead malfunction rarely results in significant morbidity, the presence of a lead stiffener wire fracture represents a threat to the patient. Physicians have, in the past, been faced with a difficult choice: whether or not to remove a functioning lead with an inherent potential for serious morbidity, or risk lead extraction. Lead extraction may have a risk of serious complication of 2.5% and a mortality of 0.6%, while the risk of retaining the lead is unknown but presumably persists as long as the lead remains in situ. Smith et al., "Five-Years Experience With Intravascular Lead Extraction," PACE 1994; Vol. 17, Pt. II, Pg. 2016 et seq.

Where lead-related complications require lead removal (lead extraction), a number of techniques have been used. Initially, only patients with life-threatening complications such as septicemia were considered candidates for lead removal. The risk and morbidity of extracting the leads had to be weighted against the medical risk and morbidity of leaving them in place.

Extraction techniques have ranged from simple procedures requiring only a few minutes under local anesthesia to complicated procedures lasting hours under general anesthesia. Lead extraction is potentially dangerous. Complications include failure to extract an infected lead, low cardiac output, lead breakage and migration, avulsion of veins and myocardial tissue (e.g, muscle, tricuspid valve), and tears of the veins and heart wall with hemothorax, tamponade, and death.

All current lead extraction procedures use some form of traction. Counteraction is applied through the implant vein using an superior vena cava approach and indirectly through the femoral vein using an inferior vena cava approach. Pulling on the lead was a successful method of extracting the lead during the early years of pacing, when leads lacked efficient fixation devices and were implanted for short periods of time. Traction may be unsafe and have a high incidence of failure when applied to leads with efficient fixation devices and leads implanted for longer periods of time. Failure to extract a lead frequently damages the lead, making future extraction attempts more difficult.

While it is possible to introduce additional insulation or cladding throughout the length of the lead to prevent the threat of fracturing, this is not routinely done. Surgical practice indicates that thicker leads tend to be stiffer and more difficult to place in the restricted cavities and channels of the body. For this reason, the modern trend is to make such leads as thin as reasonably possible. This trend heightens the possibility of lead failure, breakage and shorting.

Devices are needed which can be positioned over lead sections which are known to be flawed or which are at risk of failure. Particularly, such lead repair devices are needed which can protect a patient with an implanted cardiac stimulator whose flawed lead represents a threat to health or life if left unrepaired. Preferably, such devices will be able to be positioned at various points along the length of a lead at the discretion of the heart surgeon. Such devices will be of particular usefulness if they can repair or protect a patient whose lead wire stiffener has fractured or where a defibrillation lead might unwind upon retraction, worsening prognosis for removal of the lead.

SUMMARY OF THE INVENTION

The present invention provides devices and methods for using such devices which can be positioned over lead sections which are known to be flawed or which are at risk of failure. The devices and methods of the invention can protect a patient with an implanted cardiac stimulator whose flawed lead represents a threat to his health or life. The devices and methods of the invention provide movable sleeves which can be positioned at various points along the length of a lead at the discretion of the heart surgeon. In an important embodiment of the invention, the devices and methods are capable of facilitating the repair of leads in patients whose lead wire stiffener has fractured.

Generally, a lead repair device is disclosed which comprises a sleeve. The leads of the invention are of a type routinely utilized as implantable cardiac stimulator leads (pacemakers and cardioverter-defibrillators). Thus, the leads may be those which require surgery to expose the myocardial tissue whereby an electrode is affixed to the epicardial tissue. They may also be of the type which can be inserted through a body vessel such as a vein into the heart where an electrode attached thereto may contact the endocardial tissue. In the later type, the lead is often secured to the heart through the endothelial lining by wire helices, hooks, or tines affixed to a distal end of the lead.

In most cases, an endocardial lead will outlast its associated implanted device. However, the lead may become inoperative or another type of lead may be needed by the patient after a time. When this happens, the existing lead is typically left in place and an additional lead is implanted, rather than risk removal of the old lead, now bonded to the surrounding tissue. However, where a defect in the lead such as fracture of the stiffener wire has occurred, leaving the inoperative lead in place can raise substantial risk of injury to the patient if the lead fracture is left unrepaired. A similar problem arises in the removal of defibrillation leads in which exposed wound wires (typically as much as a 2.0 inch length of coiled wire at the distal end of the lead) tend to become unwound when backed out of the heart and vessel. It is a principal goal of the devices and methods of the invention to facilitate all such repairs.

The sleeve is generally one which is hollow or which has an internal bore throughout the long dimension of the cylinder. It also has a length substantially less than the length of the lead. The sleeves of the invention will typically be no longer than necessary to cover the section of the lead requiring repair or preventative maintenance. It other cases, especially where such sleeves are routinely fitted onto newly implanted leads without a presently known need for repair or maintenance, the sleeve may be of a longer length in order to accommodate unknown lengths of lead section repair. In these instances, the pre-fitted sleeve may be one which can be sectioned into various lengths prior to positioning. In any case, the sleeve length when compared to the length of the lead overall will be a small ratio.

The sleeves of the invention are also those having internal diameters which are substantially the same as the outer diameter of the leads on which they are to be used. This similarity in diameters is in one regard responsible for the ability of the sleeve to exclude fluids from body tissues from the interface between the internal surface of the sleeve and the external surface of the lead, in certain embodiments. Thus, for purposes of the invention, the substantial similarity in these two dimensions is such that the sleeve will be capable of tightly fitting the lead when positioned over the section of the lead requiring repair or maintenance. However, where, in certain embodiments, the sleeve is not first placed in a temporary expanded configuration for ease of positioning, the substantially similar diameters of the internal sleeve and the external lead are such that the sleeve may be slidably positioned along the lead.

The sleeves of the invention are also those capable of being threaded onto the lead. In one regard, this capability is provided by the internal bore or hollow space of the sleeve which is constructed in order to matingly receive the lead throughout its length. In another regard, this capability is provided by the dually open-ended cylinder comprising the sleeve, such construction allowing the lead to protrude in both directions from the sleeve cylinder.

The sleeves of the invention are also capable of being movably positioned over a section of the lead in order to repair or prevent further damage from a defect in the lead. Once threaded onto the lead, the sleeves of the invention may be moved in either direction along the length of the lead in order to provide the surgeon discretion as to placement along the lead length. In most instances, the surgeon will have conducted pre-operative fluoroscopy in order to localize and isolate a section of an implanted lead which exhibits a flaw. Having localized the flawed section, the surgeon will then move the sleeve into a position over that section of the lead exhibiting the flaw. In doing so, the surgeon can again use fluoroscopy to position and confirm the placement of the sleeve over the situs in need of repair or maintenance. In certain instances, it may be desirable to impregnate the sleeves with a fluoroscopically-detectable (x-ray opaque) marker or substance to facilitate the ability of the surgeon to "see" the sleeve in relation to its proper position.

Such sleeves may be used both for repair of presently flawed leads which, without such repair, are not functional. The sleeves may also be used for maintenance purposes where, while no presently inoperative flaw exists, it is anticipated that a flaw in the lead may develop. Such a preventative use of the sleeves of the invention are likely where leads come into close proximity with an abrasive surface such as a bone, or where such leads are tortuously bent at angles causing likely excessive wear.

The sleeves of the invention may be constructed of a variety of materials. It is preferred that such materials be biocompatible, meaning that they substantially lack inflammatory, immune system induction, and other undesirable biological reactions. Certain biocompatible materials useful for constructing the sleeves of the invention are the various silicone elastomers known well to those of skill in the art of cardiac stimulators and leads. The biocompatible material may also be any of the flexible polyurethanes known well to those of skill in the art of cardiac stimulators and leads. These polymeric, plastic materials will be of particular usefulness where it is desired that the sleeve be capable of excluding substantially all fluids from the section of the lead. Such instances will include those where it is desired to insulate the lead electrically from the tissue fluids.

In other instances, the sleeve will comprise a metallic wire stent-like construction. Classical cardiovascular stents are inserted into a vessel in a compressed configuration and are released to assume an expanded configuration in order to hold open a conduit. As opposed to the classical stent used in cardiovascular surgery, however, the "stents" useful in the invention will be ones whose memory position is such that the stent tightly encompasses the lead when it is in place over the repair site. These type stents will be capable of assuming an expanded configuration in which the internal diameter of the sleeve is temporarily greater than the outer diameter of the lead. When in place over the site to be repaired, such stents will be relaxed and allowed to assume the compressed memory position.

In one embodiment, the stent is held in the expanded configuration by a water-soluble coating. The coating is one which is rigid enough to maintain the stent in its expanded configuration for at least long enough to position the stent over the site to be repaired. Thus, in one embodiment the stent coating may itself be a sleeve, commensurate with the definition of such in this invention, which may be fitted on its outer surface with the expanded configuration stent. The water-soluble nature of the coating for purposes of the invention is such that the coating is capable of gradually dissolving in the presence of body fluids over a time period which would at least allow positioning of the stent over the area to be repaired. Longer dissolution periods may find usefulness where it is necessary for the surgeon to repeatedly adjust the position of the sleeve, such as where fluoroscopic confirmation of correct positioning is necessary. The water-soluble coating may be constructed out of any number of such water-soluble substances including gelatin and other polysaccharides such as starches, dextrans and the like, proteins, sugars, and salts. Where such coatings are used, it will be important to provide access of the body fluids to the coating such as through pores, which pores are at least open long enough to allow adequate dissolution of the coating.

The metallic wire stents of the invention will be made of a metal, such as a type of stainless steel. Metals of particular usefulness will be thermal-shaped memory alloys, such as nitinol. These metals provide the advantage that at lower temperatures, they may be temporarily configured in an expanded form. As these metals are warmed by the body, they may be configured to return to a memory position which is compressed to tightly conform to the outer diameter of the lead, when placed in position over the site to be repaired. Another useful metal for the stents of the invention would be tantalum.

The metallic wire stents of the invention may be coated, such as with a flexible polyurethane coating. This embodiment allows otherwise non-insulating stents to be capable of excluding body fluids from the repaired section of the lead.

In other embodiments, the sleeves of the invention may further comprise suture attachment structures on the outer surface of the sleeve. In certain configurations, these suture attachment structures will consist of a plurality of grooves circumscribing the sleeve, such as those routinely found in immovable suture sleeves on implantable leads. The suture attachment structure may also consist of a plurality of tabs or wings with openings through which sutures may be threaded. In these latter embodiments, prior to positioning the sleeve for purposes of lead repair, it may be desirable to remove the tabs or wings in order to facilitate movement of the sleeve along the lead.

The sleeves of the invention may further comprise lead attachment structures capable of preventing dislodgement of the sleeve from the repaired section of the lead. These structures may take the form of crimps, barbs, hooks, or tines on the inner surface of the sleeve in proximity to the outer insulating layer of the lead. Where the lead attachment structure is a barb, hook, or tine, it will be capable of penetrating the surface insulation of the lead. However, such penetration will be of an extent and nature so as to not substantially weaken the lead or its insulating layer.

Other means of affixing the sleeve to the lead may be used, as well. A suitable adhesive may be included in between the inner surface of the sleeve and the outer surface of the lead. Such an adhesive will be one capable of delayed affixation only after the sleeve is in position over the section to be repaired. The sleeve may be constructed out of a heat-shrinkable material such as shrink-wrap plastics or the like. In such embodiments, the tools used to position the sleeve will also be capable of heating the sleeve suitably to induce shrinkage of the sleeve tightly around the lead. It is also possible to prefabricate the lead with a series of evenly-spaced ribs around the circumference of the outer surface of the lead insulation at various points along its lengths. In such an embodiment, these ribs will be designed to articulate with similarly-sized and spaced, mated receptacles on the interior surface of the sleeve. The size and spacing of the ribs and receptacles will be of a nature to allow translocation of the sleeve along the lead, but will also present enough of a profile and mating interaction to resist movement of the sleeve when in its final destination along the lead, and will also provide the necessary sealing effect to exclude fluids from the lead/sleeve interface. It will be recognized by those of skill in the art of lead manufacture, that isodiametrical leads of uniformly thin cross section are desirable. Thus, where ribbed leads are to be used, the profiles of the ribs presented when initially positioning the lead into the vessels, valves and cavities of the heart should be minimized.

The devices of the invention are chiefly designed to repair or otherwise maintain the integrity and operability of a lead subject to a defect or flaw. A variety of defects or flaws will be amenable to the sleeves of the invention. In certain instances, the defect will comprise a flawed wire lead stiffener. Where such a defective stiffener is detected, it may be found in a condition in which it has not yet breached the insulating layer of the lead. In these instances, positioning of the sleeve will be accomplished in any of the manners and with any of the devices as disclosed herein. In other instances, the lead wire stiffener may be found to have breached the insulating layer and be protruding from the lead. In these instances, the choice of sleeve will be limited to those that may be fitted over such protruding wires, such as the expanded configuration stent-type sleeve. In the instance of defibrillation leads, a common defect involves uncoiling of an outer wire coil on such leads.

Other defects amenable to the devices of the invention include those comprising a short in the lead or actual breakage of the lead wire. Such shorts typically arise as a result of a breach in an insulator coating on the lead. Where a short is to be repaired in order to make the lead operable or to ensure its continuing electrical conduction, those sleeves as disclosed herein which create watertight seals between the sleeve and lead are preferred.

In certain embodiments of the sleeve devices of the invention, the sleeve will be fitted over the proximal end of the lead. In typical lead extraction surgery or where leads are to be left in place but disconnected from the cardiac stimulator, for instance, the lead is severed in a location distal to the connectors and other structures in order to provide a uniformly unobstructed lead surface for extraction. In those instances, it will be possible to simply thread the sleeves of the invention onto the lead and thereafter position them along the lead to the section to be repaired.

However, in most instances in which the connectors or other structures fixedly attached to the lead are to be left in place, it will be necessary to utilize sleeves which have openings or slots along the entire length of the cylinder. This will also be the case where, as is common in certain types of implanted devices, the lead is bifurcated near the proximal end of the lead. In these embodiments, the opening or slot will have a width substantially the same as or less than the outer diameter of the lead, allowing thereby the lead to pass through the slot and be encompassed by the sleeve. In these instances, the opening will be capable of allowing the sleeve to be fitted onto the lead at a position intermediate proximal and distal ends of the lead, regardless of the presence of the proximally-located connectors and other obstructions. The opening or slot may be one which is parallel to the long dimension of the sleeve. The slot or opening may also be of a coiled-ribbon nature in which the slot comprises one or more helical turns from one to the other end of the sleeve. The two sides of the slot or opening may be spaced apart from one another. Alternatively, and preferably where it is desirable to form a sealed joint, the sides may abut or overlap one another tightly. The faces of the two sides of the slot or opening of the sleeve may be parallel to one another and to the diameter of the cylindrical sleeve. In other instances, especially where the two sides of the opening or slot are to be tightly mated, the faces may be parallel to one another, but angled in relation to the cylindrical diameter. In another embodiment, paired-slotted sleeves may be used in which an outer slotted sleeve and an inner slotted sleeve have their slots brought into register to fit them onto the lead. After fitting into the sleeve, the slots on the two sleeves are placed out of register in order to seal the paired sleeves.

Other constructions utilizing the sleeves of the invention will comprise a sleeve which is fitted onto the lead prior to or contemporaneously with implantation of the lead. In these instances, the sleeve is an integral part of the implanted lead, much as is the connector and suture attachment structure. Typically, it will remain proximally located near the connector until such time as it is needed for repair or maintenance, at which time it may be used in the manner disclosed herein for sleeves affixed to the lead after implantation.

In other instances, where the obstructions such as the connectors and suture attachment structures are of a profile which presents a de minimal expansion of the outer diameter of the lead, sleeves which are sufficiently flexible to be threaded onto the lead proximal to connectors and suture attachment structures affixed to the lead may be used. These flexible sleeves may be slidably passed over the connectors and suture attachment structures to assume a position distal to the connectors and suture attachment structures.

Thus, in preferred embodiments, the sleeves of the invention will be biocompatible, capable of sliding over the lead, capable of tightening onto the lead at the desire location, capable of conforming to the lead radii, resistant to mechanical or fluid penetration, visible fluoroscopically, small enough in diameter to pass through a vein and to be retracted with the lead later, and of a design that will not further weaken or abrade the lead over time.

A method of repairing leads using the above devices is also disclosed. The general method is initiated by constructing one of the hollow cylindrical sleeve devices of the invention, with a length substantially less than that of the lead, and an internal diameter substantially the same as the outer diameter of the lead. Next, the selected sleeve is fitted onto the lead such as by threading. After the sleeve is fitted onto the lead, it is placed along the lead at a position proximal to a section of the sleeve subject to or experiencing a defect. Finally, the sleeve is positioned over the damaged section of the lead in order to repair or prevent further damage from the defect in the lead and affixed to the lead.

In certain instances, the methods of the invention will position the sleeve by slidably moving the sleeve along the lead length with a flexible tube slidably surrounding the lead proximal to the sleeve. Much like a hollow drinking straw, the hollow tube is used as a blunt-ended driver to push the sleeve down the shaft of the lead. The tube is one having an internal diameter less than an outer diameter of the sleeve but greater than the outer diameter of the lead, so that the tube can effectively shove against the proximal end of the sleeve and move it. Such a tube system requires the removal of all obstructions along the proximal terminus of the lead such as the lead connector and the proximal suture attachments structures.

A hollow tube such as a lead extractor sheath is suitable for use as the tube for moving the sleeve into place. In particular, a telescoping lead extractor sheath will find use, because such a telescoping tube may be used to move the sleeve through increasingly smaller and tighter restrictions and cavities as the sleeve approaches the most distal ends of the lead.

In a modification of the method of using a hollow tube to position the sleeve, a telescoping lead extractor sheath may be used by fitting at a distal-most terminus of the sheath, the sleeve in an expanded configuration. Thus, if the sleeve to be used is a flexible silicone elastomer sleeve, it is stretched to fit over the smallest end of the sheath. The next proximal-most sheath tube is selected to be capable of abutting the sleeve and dislodging from the terminal end of the smaller sheath tube section onto the lead. The telescoping sheath is moved along the lead to the section to be repaired. The sleeve is dislodged from the distal-most terminus of the sheath to assume a contracted position on the lead at the repaired section.

In another embodiment, the tube is a coiled, flexible ribbon. Such a device is disclosed in U.S. patent application, Ser. No. 08/428,450, filed Apr. 25, 1995, assigned to the assignee of the present invention. That system does not require the removal of the obstructions that would prevent use of a rigid walled tube as described above. Rather, the coiled flexible ribbon is wrapped around the lead proximally to the sleeve, by twisting the coil around the lead with a portion of the lead protruding between turns of the coil. By turning the coil, the coil can be carefully advanced along the lead toward the distal end thereof. In so doing, the sleeve is slidably moved toward the section requiring repair.

Of course, the method may also be used with a slotted sleeve. In this embodiment, the sleeve is placed along the lead by inserting the lead into an opening along the sleeve's entire length. As described above, the slot or opening has a width substantially the same or less than the outer diameter of the lead, allowing the sleeve to be fitted onto the lead at a position intermediate proximal and distal ends of the lead.

Where necessary, the methods of the invention provide for lubricating the sleeve prior to the positioning step in order to facilitate the positioning.

BRIEF DESCRIPTION OF THE DRAWINGS

FIG. 1. A. Cardiac stimulator lead with flawed distal end and with proximally placed obstructions requiring use of a coiled ribbon extraction sheath to position repair sleeve. B. Placement of repair sleeve over flawed section of lead.

FIG. 2. Alternative sleeve constructions to accommodate proximal connector or suture sleeve obstructions. A. Flexible repair sleeve capable of being slidably moved over obstruction. B. Slotted repair sleeve capable of being placed on lead without interacting with proximal obstructions.

FIG. 3. Alternative sleeve constructions providing for suture attachments A. Winged or tabbed suture attachment structures on repair sleeve. B suture attachment structures on repair sleeve.

FIG. 6. Helically-woven wire stent-type repair sleeve. A. Expanded configuration. B. Collapsed memory-configuration.

FIG. 7. Alternative stent-type repair sleeves. A. Chain-link wire mesh. B. W-shaped wire. C. Diamond-shaped wire mesh.

DESCRIPTION OF PREFERRED EMBODIMENTS

Figure 1A:
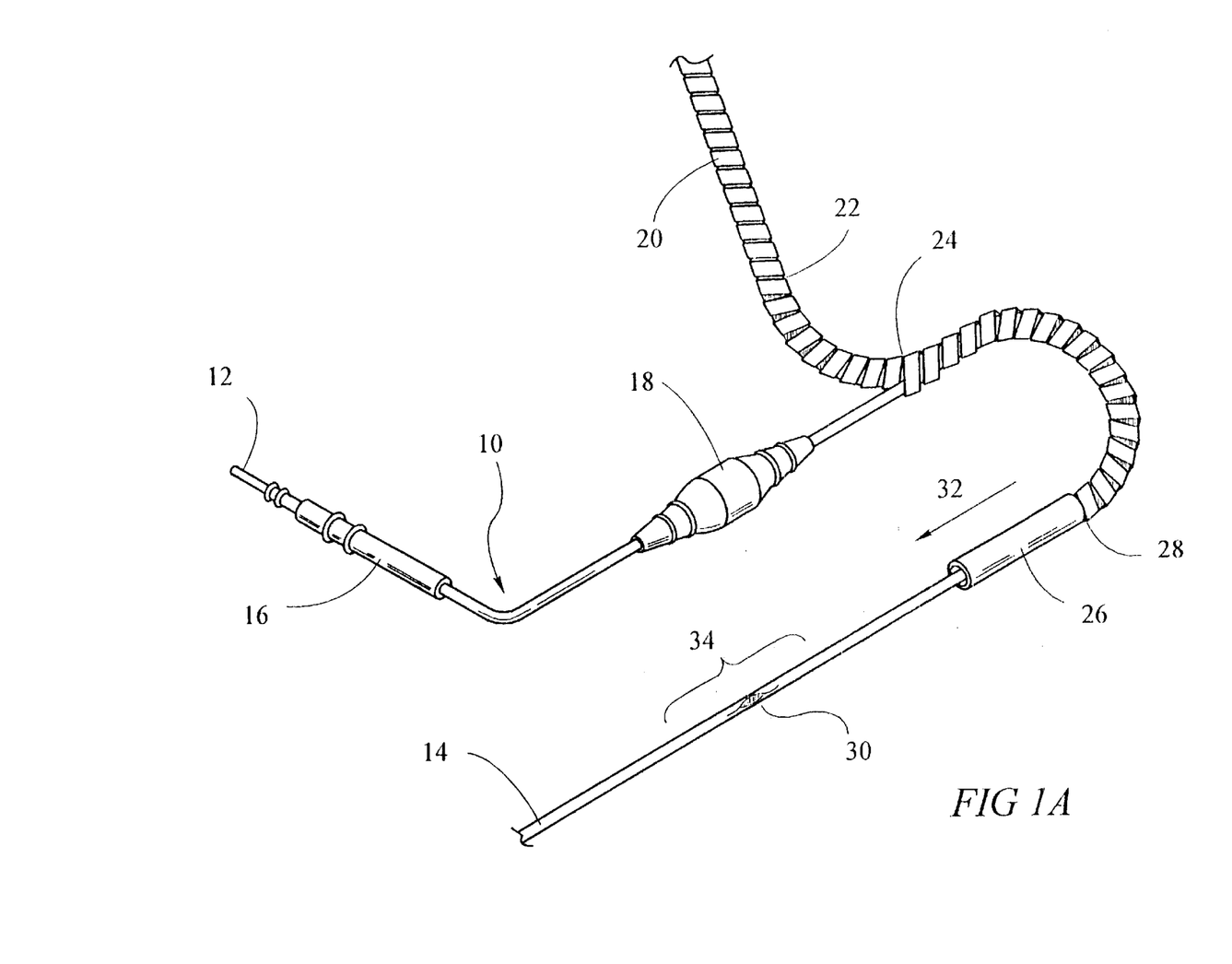
Figure 1B:
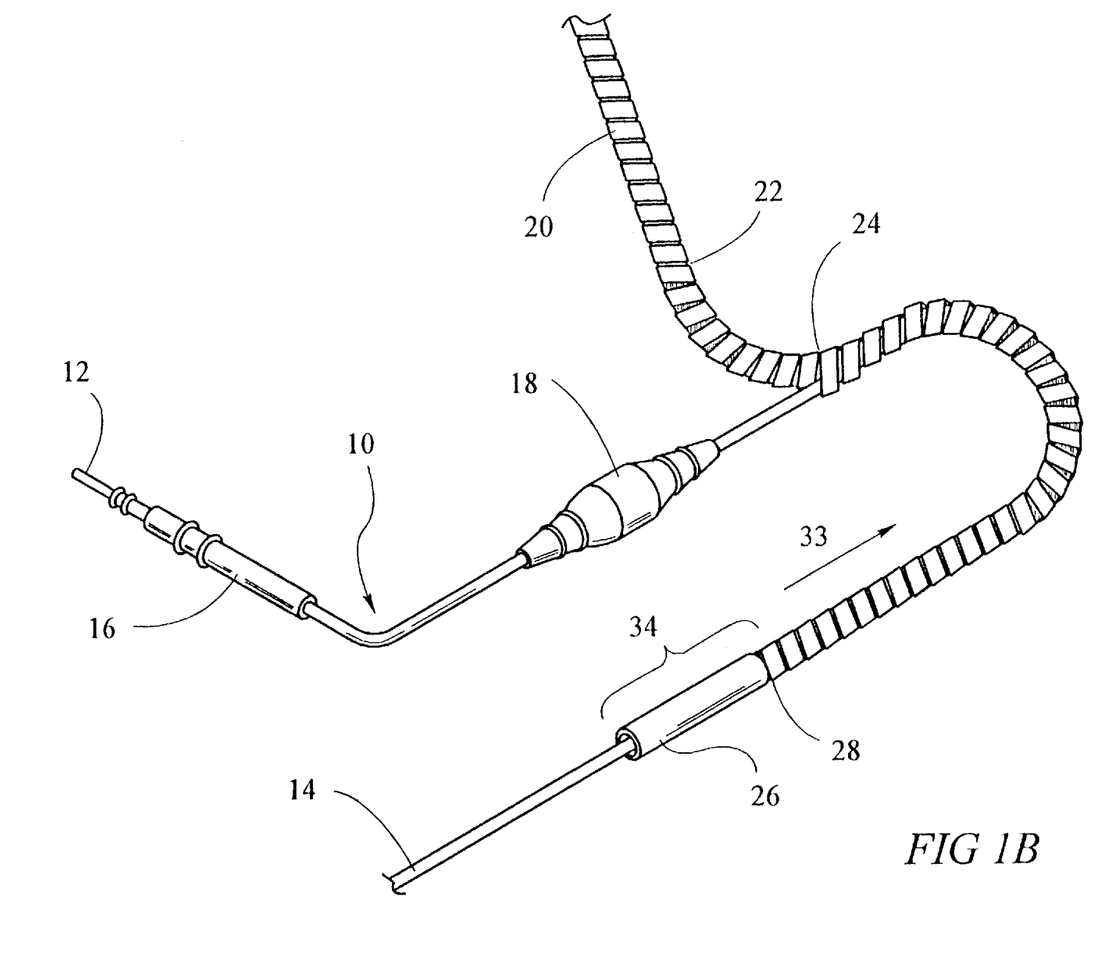

Referring now to the figures, in FIG. 1A and B, a section of an implanted lead is repaired. FIG. 1A depicts lead 10 with proximal end 12 and distal end 14. Lead 10 has been diagnosed as having a flaw 30, such as a breach in the lead insulation causing a short, in a section 34. The lead is still capable of operation if covered with a sleeve sufficiently watertight to prevent flaw 30 from contacting body fluid. Repair sleeve 26 has been fitted onto lead 10. Since proximal end 12 possesses lead connector 16 and suture attachment structure 18, both of which represent obstructions of sufficiently large profile to allow simple threading of sleeve 26 onto lead 10, sleeve 26 is slotted (not shown) and is installed onto lead 10 distal to suture attachment structure 18. Coiled-ribbon lead extractor sheath 20 with spacing 22 between the ribbon coils is inserted at position 24 proximal to sleeve 26 but distal to suture attachment structure 18. The distal-most end of coiled ribbon 20 abuts the proximal-most end of sleeve 26 at position 28. By applying force in the direction of vector 32 at position 28 through twisting of more coils of coiled-ribbon 20 onto lead 10, sleeve 26 is slidably moved distally along lead 10 toward section 34 where flaw 30 has been localized. FIG. 1B depicts sleeve 26 in place over section 34. Pressure at position 28 is relieved by reversing the direction of twisting of coiled-ribbon 20 and retracting same along vector 33, leaving in place sleeve 26. In certain cases, an additional outer sheath (not shown) may be used to widen the vein as required. Also, the inside of sleeve 26 may be lubricated to ease movement along lead 10.

Figure 2A:
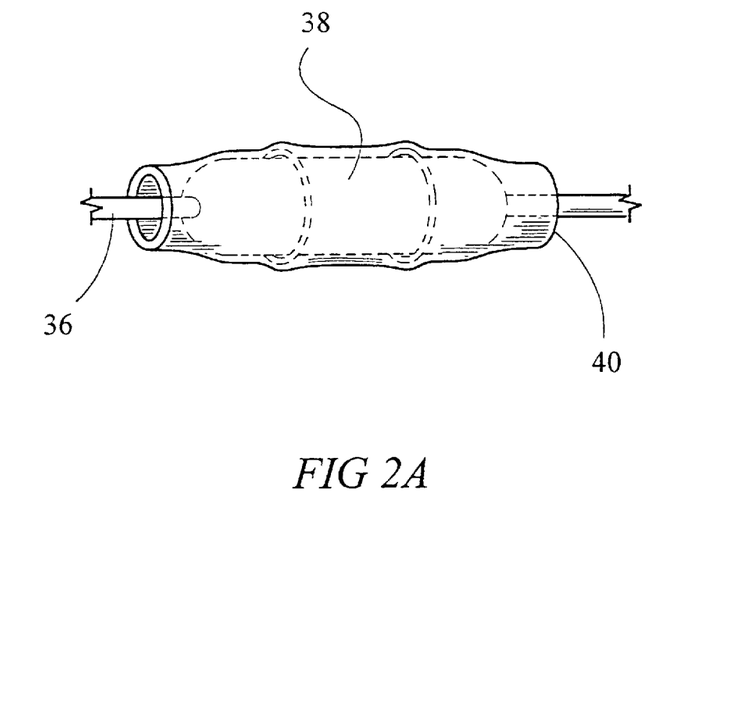
Figure 2B:
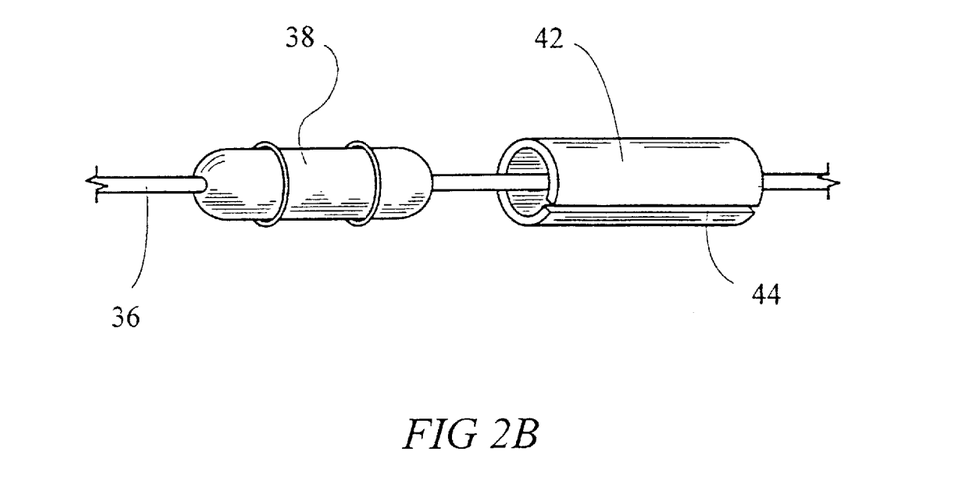

FIG. 2A and B depict alternative sleeve constructions for use where proximal obstructions are left undisturbed on the lead. In each case, lead 36 has fixedly attached to it lead connector 38. In FIG. 2A, sleeve 40 is constructed of a flexible enough material to allow it to be slidably moved in a distal direction along lead 36 over lead connector 38. After passing lead connector 38 (not shown), flexible sleeve 40 is sufficiently resilient to return to a collapsed configuration suitable for fitting lead 36 for purposes of repair. Alternatively, in FIG. 2B, slotted sleeve 42 is fitted onto lead 36 distally to connector 38 through slot 44. In either case (FIG. 2A or 2B), sleeve 40 or 42 is pushed down lead 36 as illustrated in FIG. 1A and B.

Figure 3A:
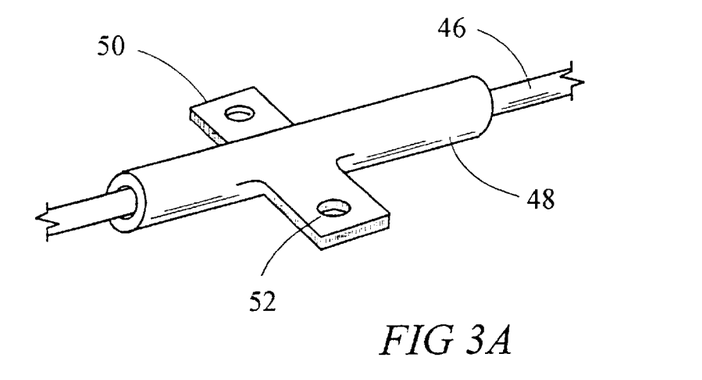
Figure 3B:
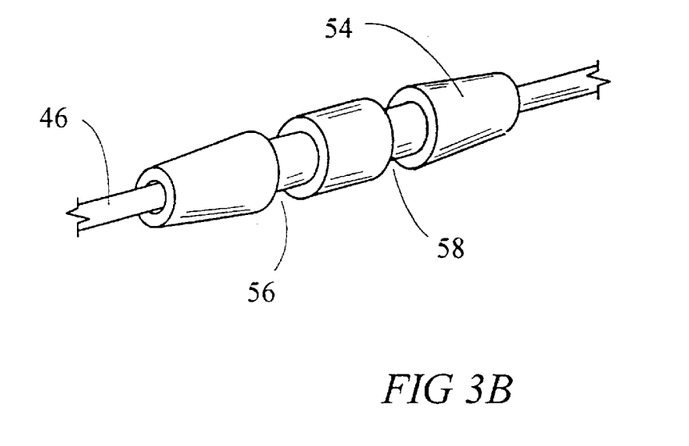

In certain embodiments, the lead is designed with a suture sleeve which can be moved down the lead in an emergency. FIG. 3A and B are conventional-looking suture sleeves designed to be unsutured and slid over the lead according to the present disclosure. FIG. 3A depicts winged sleeve 48 positioned on lead 46 possessing opposed tabs 50 with openings 52 for securing a suture (not shown). In use, tabs 50 will be removed prior to distally positioning the repair sleeve 48. FIG. 3B depicts another embodiment where grooved repair lead 54 is positioned along lead 46 possessing grooves 56 and 58 for securing a suture (not shown).

Figure 4:
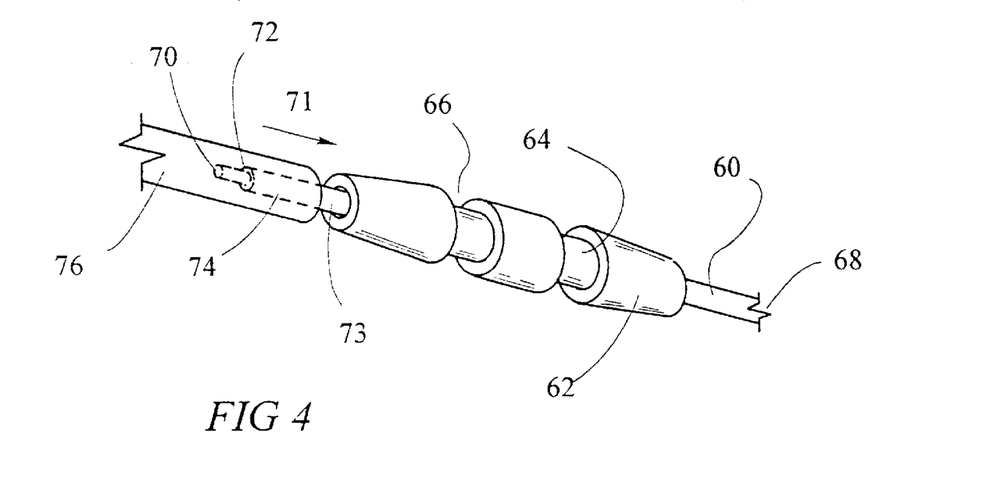
FIG. 4. Positioning of repair sleeve with grooved suture attachment structures, on a lead without proximal obstructions, using a rigid-walled extraction sheath.

The sleeves of the invention may also be pushed down the lead to the desired location using an alternative method and device as shown in FIG. 4. In this embodiment, proximal obstructions along lead 60 (not shown) have been removed, exposing lead wire 72 and lead insulation layer 74 at proximal end 70. Rigid-walled lead extraction sheath or tube 76 is inserted over lead 60 in a manner known to those versed in lead removal arts, proximal to grooved repair sleeve 62 possessing suture attachment grooves 62 and 64. Tube 76 is then used to apply pressure at position 73 along lead 60 in the direction of vector 71 in order to slidably position repair sleeve 62 distally over a section to be repaired (not shown). Tube 76 is then retracted leaving sleeve 62 over the repair site much as in the embodiment shown in FIG. 1B. Unless a connector is subsequently spliced to lead 60, lead 60 is rendered safe (for instance, from threat of wire stiffener protrusion prior to removal), but inoperative for pacing or defibrillation.

Figure 5:
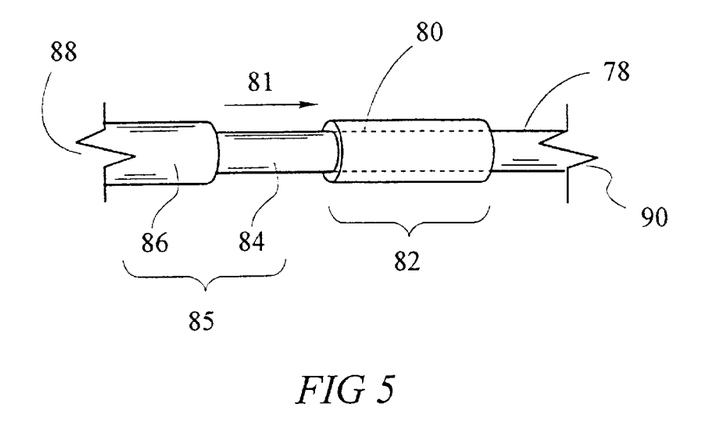
FIG. 5. A flexible repair sleeve fitted on the smallest diameter sheath of a telescoping extraction sheath and capable of being dislodged onto lead.

Another embodiment for positioning the sleeves of the invention relates to an elastic sleeve that initially covers the end of a sheath as in FIG. 5. Telescoping lead extraction sheath 85 consisting of at least narrower diameter tube 84 and wider diameter tube 86, where tube 84 is capable of slidably elongating from inside tube 86, is fitted at the distal-most end 82 of tube 84 with expandable repair sleeve 80. By slidable moving telescoping sheath 85 from proximal lead end 88 toward distal lead end 90, sleeve 80 is brought into proximity of a repair site (not shown) along lead 78. Then, sleeve 80 is either dislodged from sheath 84 by sheath 86 by applying pressure from the distal end of sheath 86 against the proximal end of sleeve 80 in the direction of vector 81, or sheath 84 is left in place with sleeve 80 and degrades or dissolves in order to release sleeve 80 onto lead 78.

Figure 7A:
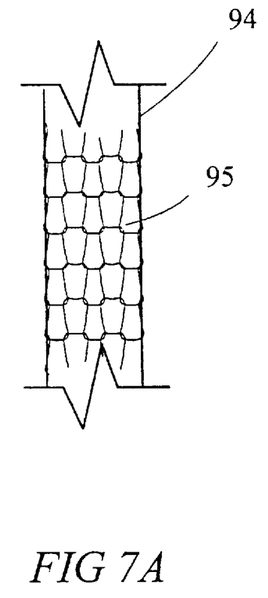
Figure 7B:
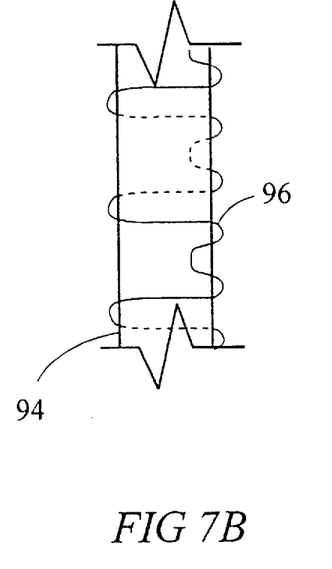
Figure 7C:
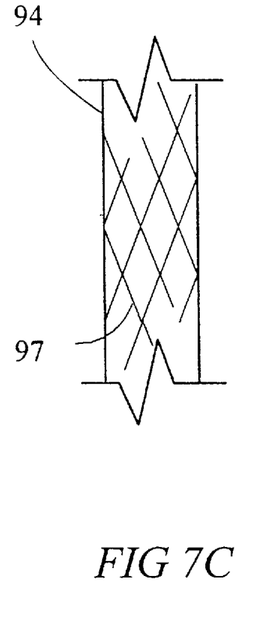
Figure 8:
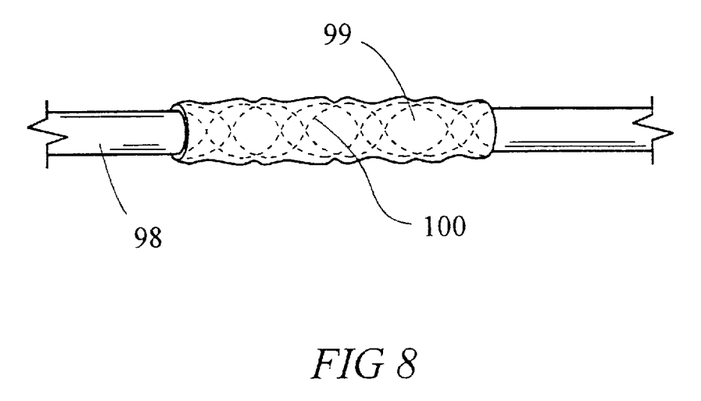
FIG. 8. Helically-woven wire stent-type repair sleeve with flexible coating.

Structures that have been used for expanding stents are amenable to the sleeves of the invention when the memory configuration is a collapsed or contracted, rather than an expanded, configuration. Examples of this type sleeve are shown in FIGS. 6–8.

Figure 6A:
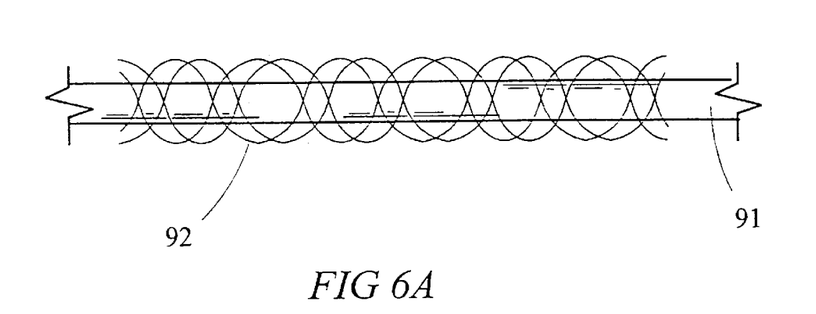
Figure 6B:
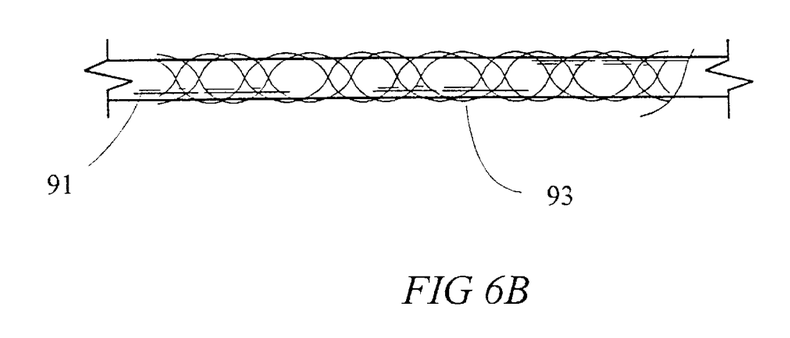

A stent-type sleeve is shown in FIG. 6A and B. A helically-woven wire mesh stent, in expanded and cooled configuration 92 is made of a memory metal material or nitinol, and is positioned initially along lead 91 proximal to a lead repair site (FIG. 6A, not shown). After positioning the stent over the repair site, it assumes its memory position 93 in response to warming at body temperature, gradually tightening over lead 91. Such sleeves will be especially useful where, as in the case of a potential stiffener wire protrusion, the sleeve does not necessarily have to insulate the lead from body fluids. In these instances, it must only form a strong cage over the lead. Of course, as with the solid sleeves discussed above, it is possible to construct such stent-type sleeves with an opening which may be closed around the lead with suitable closure mechanisms such as hooks, pins, friction strips and the like. For example, a mesh of memory alloy can be coiled around the lead distal to the connector and hooked to form a closed cylinder loose enough to slide on the lead. Alternative stent-type sleeves are shown in FIG. 5. A–C. In FIG. 7A, a chain-link wire mesh 95 is depicted. FIG. 7B depicts W-shaped wire stent 96. FIG. 7C depicts diamond-shaped wire mesh 97. The inner or outer surface of stent 100 to be placed on lead 98 may be coated or covered with a polyurethane (flexible) 99 as shown in FIG. 8.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, while the devices and methods of the invention have been described as applying to repair of cardiac stimulator leads, the devices and methods of the invention will work equally well on any implanted tubing, wiring, or other elongated device requiring repair or maintenance. Thus, where permanently implanted catheters are used, the sleeves and methods will work to repair breaches in the catheter walls. All such modifications are intended to be included within the scope of the appended claims.

What is claimed is:

1. A repair device adapted for attachment to an implantable cardiac stimulator lead situated within, or to be implanted into a person's body, and being in need of repair or protection, said repair device comprising:

a hollow cylindrical sleeve comprising a metallic wire stent capable of assuming initially an expanded configuration and finally a relaxed configuration;

said sleeve having a predetermined length substantially less than that of a conventional cardiac stimulator lead, and in said relaxed configuration having an internal diameter substantially the same as an outer diameter of a conventional cardiac stimulator lead, said relaxed configuration being one in which, at body temperature, causes the greatest amount of compression of said sleeve;

whereby upon being positioned over a predetermined section of a lead in need of protection or repair, and upon assuming said relaxed configuration, said device effectuates repair or prevents damage to said lead.

2. The device of claim 1 wherein said device is biocompatible.

3. The device of claim 1 wherein said sleeve is capable of excluding substantially all fluids from said section of said lead.

4. The device of claim 1 wherein said stent is held in said expanded configuration by a water soluble coating.

5. The device of claim 4 wherein said water soluble coating is a gelatinous substance.

6. The device of claim 4 wherein said water soluble coating is a polysaccharide substance.

7. The device of claim 1 wherein said metallic wire stent comprises stainless steel.

8. The device of claim 1 wherein said metallic wire stent comprises a thermal-shaped memory alloy.

9. The device of claim 8 wherein said thermal-shaped memory alloy is nitinol.

10. The device of claim 1 wherein said metallic wire stent comprises tantalum.

11. The device of claim 1 wherein said sleeve further comprises on its outer surface a suture attachment structure.

12. The device of claim 1 wherein said sleeve further comprises on its inner surface a lead attachment structure capable of preventing dislodgement of said sleeve from said section of said lead.

13. The device of claim 12 wherein said lead attachment structure is a barb capable of penetrating surface insulation of said lead.

14. The device of claim 1 wherein said sleeve is sufficiently flexible to be threaded onto said lead proximal to connectors and suture attachment structures affixed to said lead and slidably passed over said connectors and suture attachment structures to assume a position distal to said connectors and suture attachment structures.

15. The device of claim 1 wherein the minimum diameter of said sleeve in said expanded configuration is large enough to allow said device to be slidably positioned over a predetermined section of a conventional implantable cardiac lead.

16. The device of claim 1 wherein said stent is helically-woven wire.

17. The device of claim 1 wherein said sleeve comprises means for expanding the diameter of said sleeve and means for reducing the diameter of said sleeve.

18. A repair device adapted for attachment to an implantable cardiac stimulator lead situated within a patient's body, and having a flawed wire lead stiffener or defibrillation outer wire coil, said repair device comprising:

a hollow cylindrical sleeve comprising a metallic wire stent capable of assuming initially an expanded configuration and finally a relaxed configuration;

said sleeve having a predetermined length substantially less than that of a conventional cardiac stimulator lead, and in said relaxed configuration having an internal diameter substantially the same as an outer diameter of a conventional cardiac stimulator lead, said relaxed configuration being one in which, at body temperature, causes the greatest amount of compression of said sleeve;

whereby upon being positioned over a predetermined section of a lead in need of protection or repair, and upon assuming said relaxed configuration, said device effectuates repair or prevents damage to said lead.

19. A repair device adapted for attachment to an implantable cardiac stimulator lead situated within a patient's body, and having a lead short, said repair device comprising:

a hollow cylindrical sleeve comprising a metallic wire stent capable of assuming initially an expanded configuration and finally a relaxed configuration;

said sleeve having a predetermined length substantially less than that of a conventional cardiac stimulator lead, and in said relaxed configuration having an internal diameter substantially the same as an outer diameter of a conventional cardiac stimulator lead, said relaxed configuration being one in which, at body temperature, causes the greatest amount of compression of said sleeve;

whereby upon being slidably positioned over a predetermined section of a lead in need of protection or repair, and upon assuming said relaxed configuration, said device effectuates repair or prevents damage to said lead.

20. A method of repairing an implantable cardiac stimulator lead, comprising:

constructing a hollow cylindrical sleeve;

said sleeve having a length substantially less than that of a lead situated within, or to be implanted into a patient's body, said lead being in need of repair or protection;

said sleeve having an internal diameter substantially the same as an outer diameter of said lead;

threading said sleeve onto said lead;

placing said sleeve along said lead at a position proximal to a predetermined section of said lead subject to or experiencing a defect;

positioning said sleeve over said section of said lead and thereby effectuating repair of said lead or preventing further damage from a defect that may occur in said lead while said lead is in the patient's body; and, affixing said sleeve to said lead.

21. The method of claim 20 wherein said positioning step is accomplished by slidably moving said sleeve along said lead length with a flexible tube slidably surrounding said lead proximal to said sleeve, said tube having an internal diameter less than an outer diameter of said sleeve but greater than said outer diameter of said lead.

22. The method of claim 21 wherein said tube is a coiled, flexible ribbon.

23. The method of claim 21 wherein said tube is a lead extractor sheath.

24. The method of claim 23 wherein said lead extractor sheath is a telescoping lead extractor sheath.

25. The method of claim 20 further comprising using said telescoping lead extractor sheath by:

fitting at a distal-most terminus of said sheath said sleeve in an expanded configuration;

telescoping said sheath along said lead to said section;

dislodging said sleeve from said distal-most terminus of said sheath to assume a contracted position on said lead at said section.

26. The method of claim 20 wherein said sleeve is placed along said lead by inserting said lead into an opening along said sleeve's entire length, said opening having a width substantially the same or less than said outer diameter of said lead, said opening capable of allowing said sleeve to be fitted onto said lead at a position intermediate proximal and distal ends of said lead.

27. The method of claim 20 wherein said sleeve is lubricated prior to said positioning step in order to facilitate said positioning.

28. A method of repairing an implanted cardiac stimulator lead in situ, comprising:

threading the repair device of claim 1 onto a lead situated within a patient's body, said lead being in need of repair or protection;

placing said device along said lead at a position proximal to a section of said lead subject to or experiencing a defect;

positioning said device over said section of said lead; and     affixing said device to said lead.

29. A method of protecting an implantable cardiac stimulator lead, comprising:

threading the repair device of claim 1 onto a lead, said device being adapted for being fitted onto said lead prior to or contemporaneously with implantation of said lead;

placing said device along said lead at a position proximal to a section of said lead subject to occurrence of a defect while implanted;

positioning said device over said section of said lead; and     affixing said device to said lead.

\* \* \* \* \*